(12) United States Patent
Evans et al.

(10) Patent No.: US 11,457,949 B2
(45) Date of Patent: Oct. 4, 2022

(54) SURGICAL ACCESS DEVICE AND SEAL GUARD FOR USE THEREWITH

(71) Applicant: Covidien LP, Mansfield, MA (US)

(72) Inventors: Christopher Kelly Evans, Southington, CT (US); Jay Breindel, Kensington, CT (US)

(73) Assignee: Covidien LP, Mansfield, MA (US)

( * ) Notice: Subject to any disclaimer, the term of this patent is extended or adjusted under 35 U.S.C. 154(b) by 150 days.

(21) Appl. No.: 16/565,902

(22) Filed: Sep. 10, 2019

(65) Prior Publication Data

US 2020/0113598 A1    Apr. 16, 2020

Related U.S. Application Data

(60) Provisional application No. 62/744,848, filed on Oct. 12, 2018.

(51) Int. Cl.
| | |
|---|---|
| *A61B 1/32* | (2006.01) |
| *A61B 17/34* | (2006.01) |
| *A61B 17/02* | (2006.01) |

(52) U.S. Cl.
CPC ...... *A61B 17/3423* (2013.01); *A61B 17/0218* (2013.01)

(58) Field of Classification Search
CPC combination set(s) only.
See application file for complete search history.

(56) References Cited

U.S. PATENT DOCUMENTS

| | | | |
|---|---|---|---|
| 3,402,710 A | 9/1968 | Paleschuck | |
| 3,495,586 A | 2/1970 | Regenbogen | |
| 4,016,884 A | 4/1977 | Kwan-Gett | |
| 4,112,932 A | 9/1978 | Chiulli | |
| 4,183,357 A | 1/1980 | Bentley et al. | |
| 4,356,826 A | 11/1982 | Kubota | |
| 4,402,683 A | 9/1983 | Kopman | |
| 4,653,476 A | 3/1987 | Bonnet | |
| 4,737,148 A | 4/1988 | Blake | |
| 4,863,430 A | 9/1989 | Klyce et al. | |
| 4,863,438 A | 9/1989 | Gauderer et al. | |
| 4,984,564 A | 1/1991 | Yuen | |

(Continued)

FOREIGN PATENT DOCUMENTS

| | | |
|---|---|---|
| CA | 2702419 A1 | 11/2010 |
| EP | 0226026 A2 | 6/1987 |

(Continued)

OTHER PUBLICATIONS

Extended European Search Report dated Jan. 9, 2020 issued in corresponding EP Appln. No. 19202763.9.

*Primary Examiner* — Sameh R Boles

(74) *Attorney, Agent, or Firm* — Carter, DeLuca & Farrell LLP

(57) ABSTRACT

A surgical access device including a cannula, a seal, and a seal guard is disclosed. The cannula includes a housing and an elongated portion extending distally from the housing. The seal is disposed at least partially within the housing of the cannula and includes an aperture for sealed reception of a surgical instrument therethrough. The seal guard is disposed at least partially within the housing of the cannula and proximally of the seal. The seal guard is formed from a flat sheet of material and folded into a funnel-like shape.

10 Claims, 4 Drawing Sheets

(56) References Cited

U.S. PATENT DOCUMENTS

| | | |
|---|---|---|
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |

(56) References Cited

U.S. PATENT DOCUMENTS

| | | |
|---|---|---|
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0187397 A1 | 10/2003 | Vitali |
| 2003/0233115 A1 | 12/2003 | Eversull et al. |

(56) References Cited

U.S. PATENT DOCUMENTS

| | | |
|---|---|---|
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0251560 A1 | 10/2011 | Albrecht et al. |
| 2011/0313250 A1 | 12/2011 | Kleyman |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Altieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2015/0223833 A1* | 8/2015 | Coffeen ............ A61B 17/3462 600/204 |
| 2018/0021063 A1 | 1/2018 | Main et al. |
| 2019/0059938 A1 | 2/2019 | Holsten |

(56) References Cited

U.S. PATENT DOCUMENTS

| | | |
|---|---|---|
| 2019/0059944 A1 | 2/2019 | Holsten |
| 2020/0246043 A1 | 8/2020 | Holsten et al. |

FOREIGN PATENT DOCUMENTS

| | | |
|---|---|---|
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| GB | 2469083 | 4/2009 |
| WO | 3401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 | 9/1997 |
| WO | 9742889 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |
| WO | 2012131746 A1 | 10/2012 |
| WO | 2014116889 A1 | 7/2014 |
| WO | 2018024101 A1 | 2/2018 |

* cited by examiner

SURGICAL ACCESS DEVICE AND SEAL GUARD FOR USE THEREWITH

CROSS-REFERENCE TO RELATED APPLICATIONS

This application claims the benefit of and priority to U.S. Provisional Patent Application Ser. No. 62/744,848 filed Oct. 12, 2018, the entire disclosure of which is incorporated by reference herein.

TECHNICAL FIELD

The present disclosure relates to a surgical access device. More particularly, the present disclosure relates to a seal guard for use with a surgical access device.

BACKGROUND OF RELATED ART

Endoscopic and laparoscopic minimally invasive procedures have been used for introducing medical devices inside a patient and for viewing portions of the patient's anatomy. Typically, to view a desired anatomical site, a surgeon may insert a rigid or flexible endoscope inside the patient to render images of the anatomical site. In endoscopic surgical procedures, surgery is performed in any hollow organ or tissue of the body through a small incision. a small opening, or through narrow endoscopic tubes (cannulas) inserted through a small incision or opening in the skin. In laparoscopic procedures, surgical operations in the abdomen are performed through small incisions (usually about 0.5 to about 1.5 cm). Laparoscopic and endoscopic procedures often require the surgeon to act on organs, tissues and vessels far removed from the opening.

Typically, a surgical access device includes a cannula and an obturator. The cannula remains in place for use during the laparoscopic procedure, and the obturator includes a tip for penetrating the body cavity. The cannula may include a seal therein (e.g., an instrument seal) to help prevent fluid and gas from entering or exiting the body through the cannula when the obturator or other surgical instrument is inserted therethrough.

Accordingly, it may be helpful to provide seal guards that are configured to help protect seals within a cannula from becoming damaged by a surgical instrument (e.g., an obturator or an endoscope), for example. Additionally, it may be helpful to provide a seal guard that has a sufficiently high strength while having a sufficiently low thickness.

SUMMARY

The present disclosure relates to a surgical access device including a cannula, a seal, and a seal guard. The cannula includes a housing and an elongated portion extending distally from the housing. The seal is disposed at least partially within the housing of the cannula and includes an aperture for sealed reception of a surgical instrument therethrough. The seal guard is disposed at least partially within the housing of the cannula and proximally of the seal. The seal guard is formed from a flat sheet of material and folded into a funnel-like shape.

In disclosed embodiments, the flat sheet of material has a thickness of about 0.001 inches.

It is also disclosed that the seal guard includes an aperture defining a star-like shape including five points.

It is further disclosed that a proximal portion of the seal guard includes a lip having at least five sections.

In disclosed embodiments, the seal guard is folded into six segments from the flat sheet of material. At least five segments of the six segments each include fold lines defining four triangles. Further, each of the at least five segments includes fold lines defining a truncated diamond shape. Additionally, the fold lines defining the truncated diamond shape of the at least five segments of the six segments are contiguous with the fold lines defining each triangle of the four triangles.

The present disclosure also relates to a seal guard for use with a surgical access device. The seal guard includes a body portion and an aperture. The body portion includes at least five segments with each segment of the at least five segments forming at least one angle with an adjacent segment. The aperture is defined by at least five points of the body portion. The seal guard is formed from a flat sheet of material folded into a funnel-like shape.

In disclosed embodiments, the flat sheet of material has a thickness of about 0.001 inches.

It is also disclosed that the aperture defines a star-like shape.

It is further disclosed that the body portion includes a lip having at least five sections.

Additionally, it is disclosed that the seal guard is folded into six segments from the flat sheet of material. At least five segments of the six segments each include fold lines defining four triangles. Further, the at least five segments each include fold lines defining a truncated diamond shape. Additionally, the fold lines defining the truncated diamond shape of the at least five segments are contiguous with the fold lines defining each triangle of the four triangles.

BRIEF DESCRIPTION OF THE DRAWINGS

Various embodiments of the present disclosure are illustrated herein with reference to the accompanying drawings, wherein.

DETAILED DESCRIPTION

Figure 1:
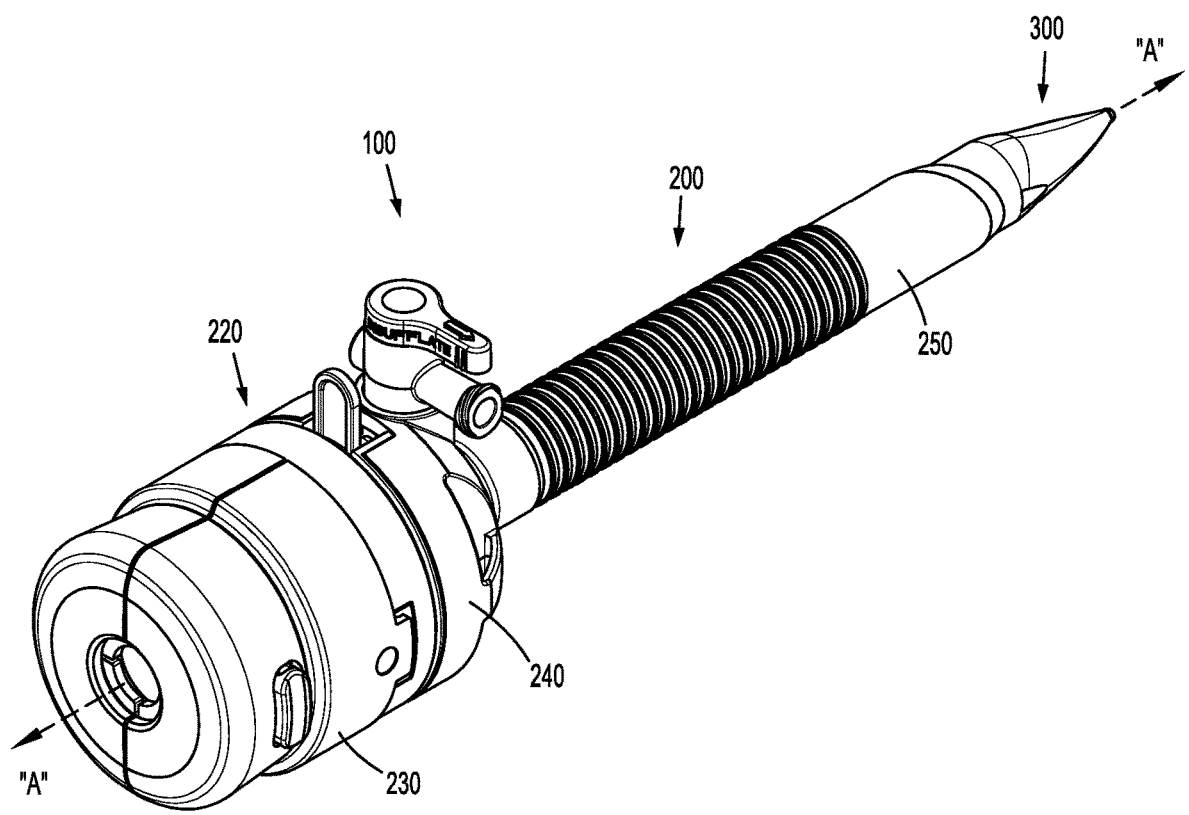
FIG. 1 is a perspective view of surgical access device including a cannula and an obturator.

Embodiments of the presently disclosed surgical access device and seal guard are described in detail with reference to the drawings, wherein like reference numerals designate corresponding elements in each of the several views.

As used herein, the term "distal" refers to that portion of the instrument, or component thereof which is farther from the user while the term "proximal" refers to that portion of the instrument or component thereof which is closer to the user.

Various embodiments of a surgical access device are described herein. Generally, the surgical access device includes a trocar assembly which may be employed during surgery (e.g., laparoscopic surgery) and may, in various embodiments, provide for the sealed access of laparoscopic surgical instruments into an insufflated body cavity, such as the abdominal cavity. As will be described in additional detail below, the trocar assemblies of the present disclosure include a cannula and an obturator insertable therethrough.

The cannula and obturator are separate components but are capable of being selectively connected together. For example, the obturator may be inserted into and through the cannula until the handle of the obturator engages, e.g., selectively locks into, a proximal housing of the cannula. In this initial position, the trocar assembly is employed to tunnel through an anatomical structure, e.g., the abdominal wall, either by making a new passage through the structure or by passing through an existing opening through the structure. Once the trocar assembly has tunneled through the anatomical structure, the obturator is removed, leaving the cannula in place in the structure, e.g., in the incision created by the trocar assembly. The proximal housing of the cannula may include seals or valves that prevent the escape of insufflation gases from the body cavity, while also allowing surgical instruments to be inserted into the cavity.

With initial reference to FIG. 1, a surgical access device 100 is shown. Surgical access device 100 generally includes a cannula 200 and an obturator 300. Obturator 300 is selectively insertable through an aperture 210 of cannula 200 and beyond a distal end of cannula 200 to create and/or enlarge an incision in tissue. Obturator 300 is then removed from cannula 200, and cannula 200 remains adjacent tissue to provide entry for additional surgical instruments therethrough. Further details of a surgical access device including a cannula and an obturator are described in U.S. Pat. No. 10,022,149 to Holsten et al., issued on Jul. 17, 2018, and U.S. Patent Application Publication No. 2018/0085145 to Okoniewski et al., filed on Nov. 13, 2017, the entire content of each of which being incorporated by reference herein.

Figure 5:
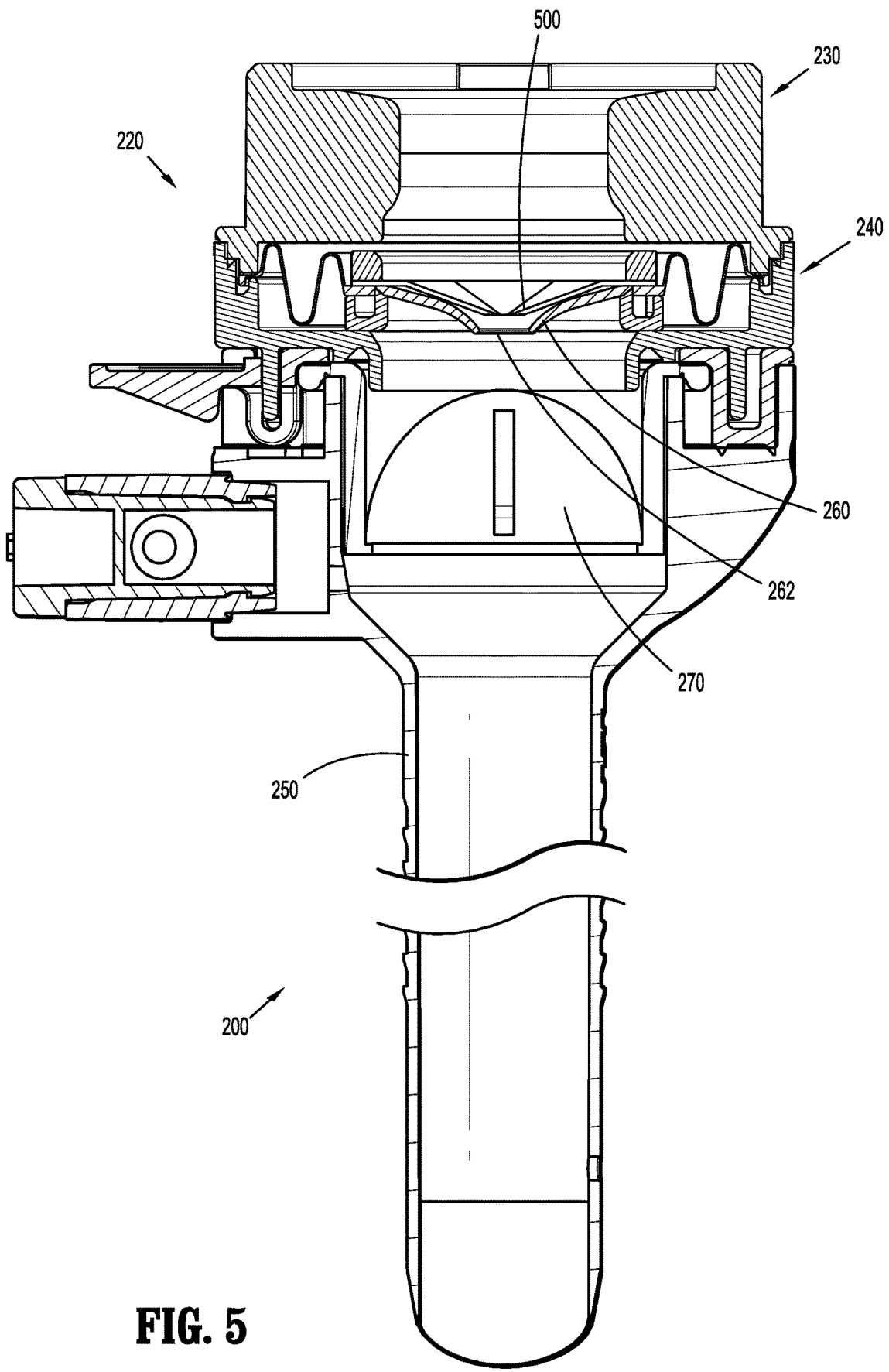
FIG. 5 is a cross-sectional view of the seal guard of FIGS. 2-4 within the cannula of FIG. 1, and with the obturator of FIG. 1 removed for clarity.

Referring to FIGS. 1 and 5, cannula 200 includes a housing 220 and an elongated portion 250 extending distally from housing 220. Elongated portion 250 of cannula 200 defines a longitudinal axis A-A extending therethrough. Housing 220 includes a proximal housing 230 that is selectively engagable with a distal housing 240. At least one seal is included within housing 220 of cannula 200. For example, an instrument seal or a septum seal 260, and/or a zero-closure seal 270 may be included within housing 200. Septum seal 260 is configured to provide a seal around the perimeter of a surgical instrument inserted through an aperture 262 of septum seal 260. Zero-closure seal 270 helps prevent the escape of insufflation gas when no instrument is present through housing 220.

During use, a distal tip of obturator 300 and/or a distal tip of a surgical device (e.g., an endoscope) inserted through housing 220 may damage septum seal 260 if inserted off-center, for instance. Accordingly, a seal guard 500 (FIGS. 2-5) is positionable proximally of septum seal 260 to help prevent a distal tip of a surgical device, such as an endoscopic surgical stapler for example, from damaging septum seal 260 as the surgical device passes through housing 220. More particularly, seal guard 500 is configured to direct or funnel a distal tip of a surgical instrument towards the longitudinal axis A-A or aperture 262 of septum seal 260 such that damaging septum seal 260 is unlikely.

Figure 2:
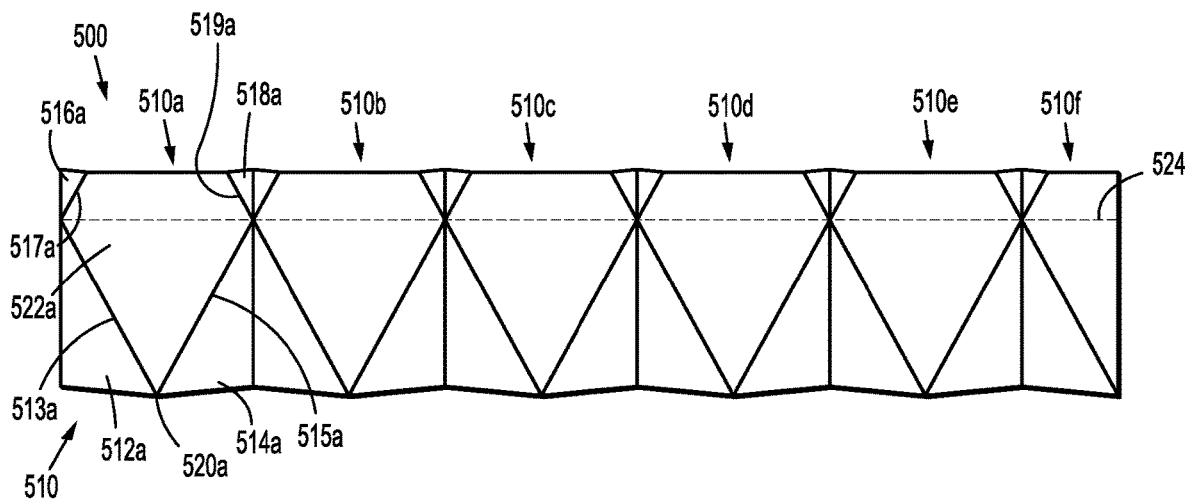
FIG. 2 is a top view of a seal guard of the present disclosure for use with the cannula of FIG. 1.
Figure 3:
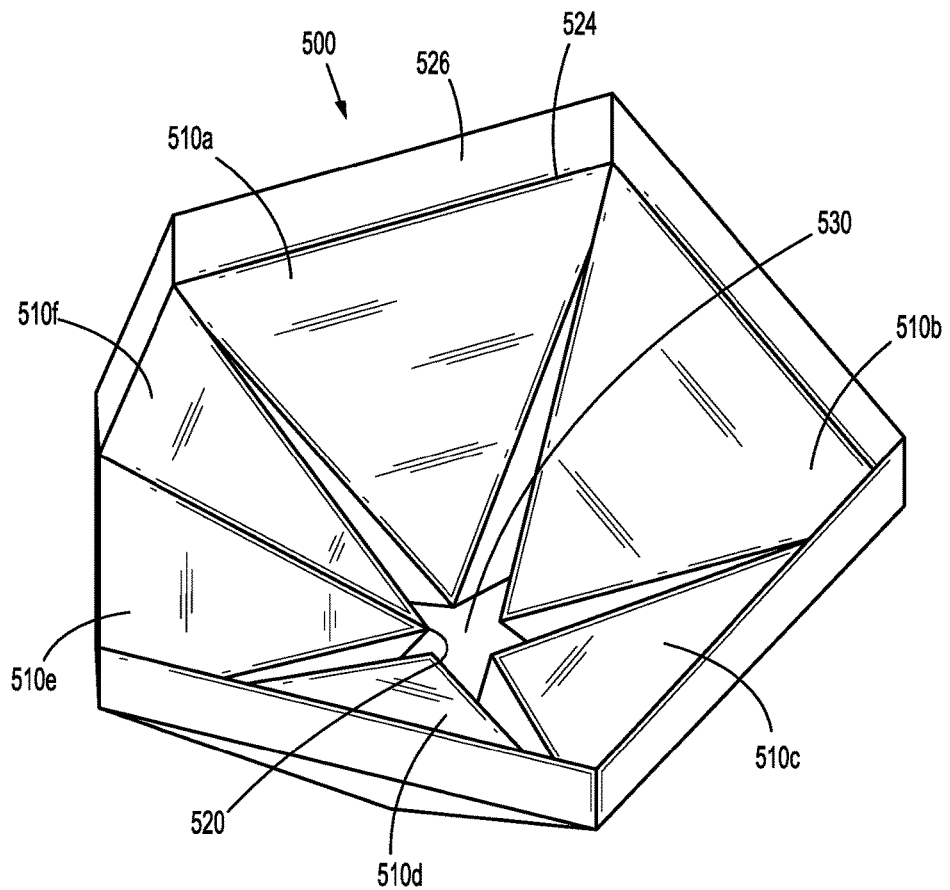
FIGS. 3 and 4 are perspective views of the seal guard of FIG. 2.
Figure 4:
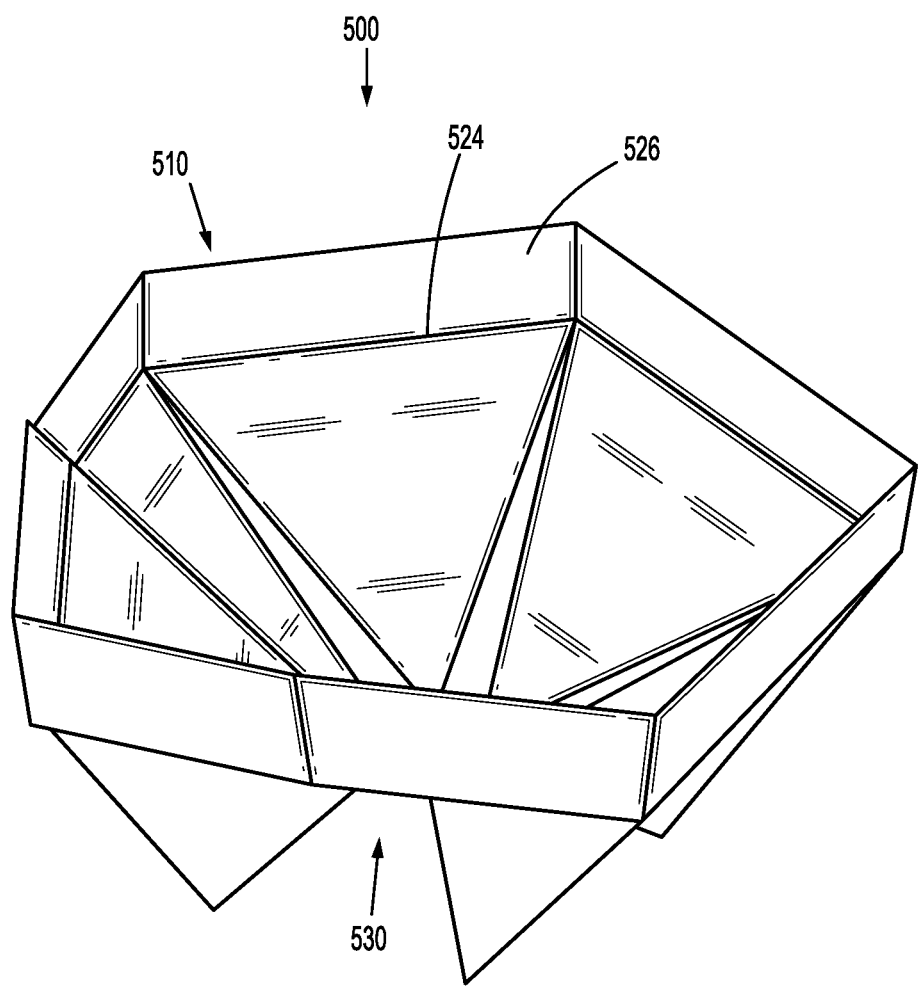

With particular reference to FIGS. 2-4, seal guard 500 is formed from a flat sheet of material (FIG. 2), and is folded into a funnel-like or frusto-conical shape (FIGS. 3 and 4). For example, seal guard 500 may be made from a flat stock or a flat sheet of a high strength plastic material. It is envisioned that the material is between about 0.0005 inches and about 0.002 inches thick. For instance, the material may be about 0.001 inches thick. Such a relatively small thickness of material can be easier to mold as compared to pre-formed seal guards having a greater thickness. Additionally, seal guard 500 includes a segmented body portion 510 and, in its folded configuration, seal guard 500 defines a central aperture 530. As shown in FIG. 3, aperture 530 defines a star-like shape (e.g., including five points).

In the illustrated embodiment, body portion 510 includes six segments 510a-510f, although a body portion 510 including more or fewer than six segments is within the scope of the present disclosure. Additionally, at least one segment (e.g., 510f) may be a different size than the other segments, as shown in FIG. 2. Here, segment 510f is approximately half of the width of the other segments 510a-510e.

Segments 510a-510f are configured to be folded in the manner shown in FIG. 2, where the lines within and between segments 510a-510f indicate fold lines. While each segment of segments 510a-510e includes the following features, only the features of segment 510a are labeled for clarity. In particular, segment 510a includes a lower left triangle 512a, a lower right triangle 514a, an upper left triangle 516a, and an upper right triangle 518a. Lower left triangle 512a is formed by fold line 513a, lower right triangle 514a is formed by fold line 515a, upper left triangle 516a is formed by fold line 517a, and upper right triangle 518a is formed by fold line 519a.

Lower triangles 512a and 514a meet at a point 520a and are larger than upper triangles 516a, 518a. Upper triangles 516a, 518a contact respective lower triangles 512a, 514a, and upper triangles 516a, 518a do not contact each other. Segments 510a-510e also include a truncated diamond shape 522a, which is contiguous to each triangle 512a, 514a, 516a, 518a.

Additionally, segments 510a-510f may each include an additional fold line 524. Folding along fold line 524 creates a lip 526 and/or defines a perimeter of seal guard 500. When seal guard 500 is in its folded position, lip 526 may define a six-sided shape, or a five-sided shape, for example. In embodiments where lip 526 defines a five-sided shape, one segment (e.g., 510f) may be fold in front of or behind another segment (e.g., 510a). Further, the two segments (e.g., 510a and 510f) may be secured to each other.

With particular reference to FIG. 3, aperture 530 is generally defined between points 520 of adjacent segments 510a-510f, for example, is configured to change shape in response to a surgical instrument being inserted therethrough. For instance, in the absence of a surgical instrument inserted through aperture 530, aperture 530 defines the smallest shape and smallest sized opening. Inserting a surgical instrument through aperture 530 causes aperture 530 to expand or enlarge. That is, for instance, points 520 move away from the longitudinal axis A-A in response to being contacted by a surgical instrument. Additionally, points 520 may be biased toward the longitudinal axis A-A such that point 520 move toward the longitudinal axis A-A after a surgical instrument has been withdrawn therefrom.

The present disclosure also includes methods of making seal guard 500 and/or assembling a surgical access device with seal guard 500. Methods include folding a flat stock of material into a funnel-like shape. Embodiments of the method also include folding the flat stock of material into a hexagonal shape, and positioning seal guard 500 within a housing of a cannula and proximally of septum seal 260, for instance.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto.

The invention claimed is:

1. A seal guard for use with a surgical access device, the seal guard comprising:
 a body portion including at least five segments, each segment of the at least five segments forming at least one angle with an adjacent segment, and each segment of the at least five segments including fold lines defining four triangles; and
 an aperture defined by at least five points of the body portion;
 wherein the seal guard is formed from a flat sheet of material folded into a funnel-like shape.

2. The seal guard according to claim 1, wherein the flat sheet of material has a thickness of about 0.001 inches.

3. The seal guard according to claim 1, wherein the aperture defines a star-like shape.

4. The seal guard according to claim 1, wherein the body portion includes a lip having at least five sections.

5. The seal guard according to claim 1, wherein the seal guard is folded into six segments from the flat sheet of material.

6. The seal guard according to claim 1, wherein the at least five segments each include fold lines defining a truncated diamond shape.

7. The seal guard according to claim 6, wherein the fold lines defining the truncated diamond shape of the at least five segments are contiguous with the fold lines defining each triangle of the four triangles.

8. A seal guard for use with a surgical access device, the seal guard comprising:
 a body portion including at least five segments, each segment of the at least five segments forming at least one angle with an adjacent segment; and
 an aperture defined by at least five points of the body portion;
 wherein the seal guard is formed from a flat sheet of material folded into a funnel-like shape, wherein the flat sheet of material has a thickness of about 0.001 inches.

9. The seal guard according to claim 8, wherein the aperture defines a star-like shape consisting of ten linear segments.

10. A seal guard for use with a surgical access device, the seal guard comprising:
 a body portion including at least five segments, each segment of the at least five segments forming at least one angle with an adjacent segment; and
 an aperture defined by at least five points of the body portion, and the aperture defining a star-like shape consisting of ten linear segments;
 wherein the seal guard is formed from a flat sheet of material folded into a funnel-like shape.

* * * * *